Figure 1:
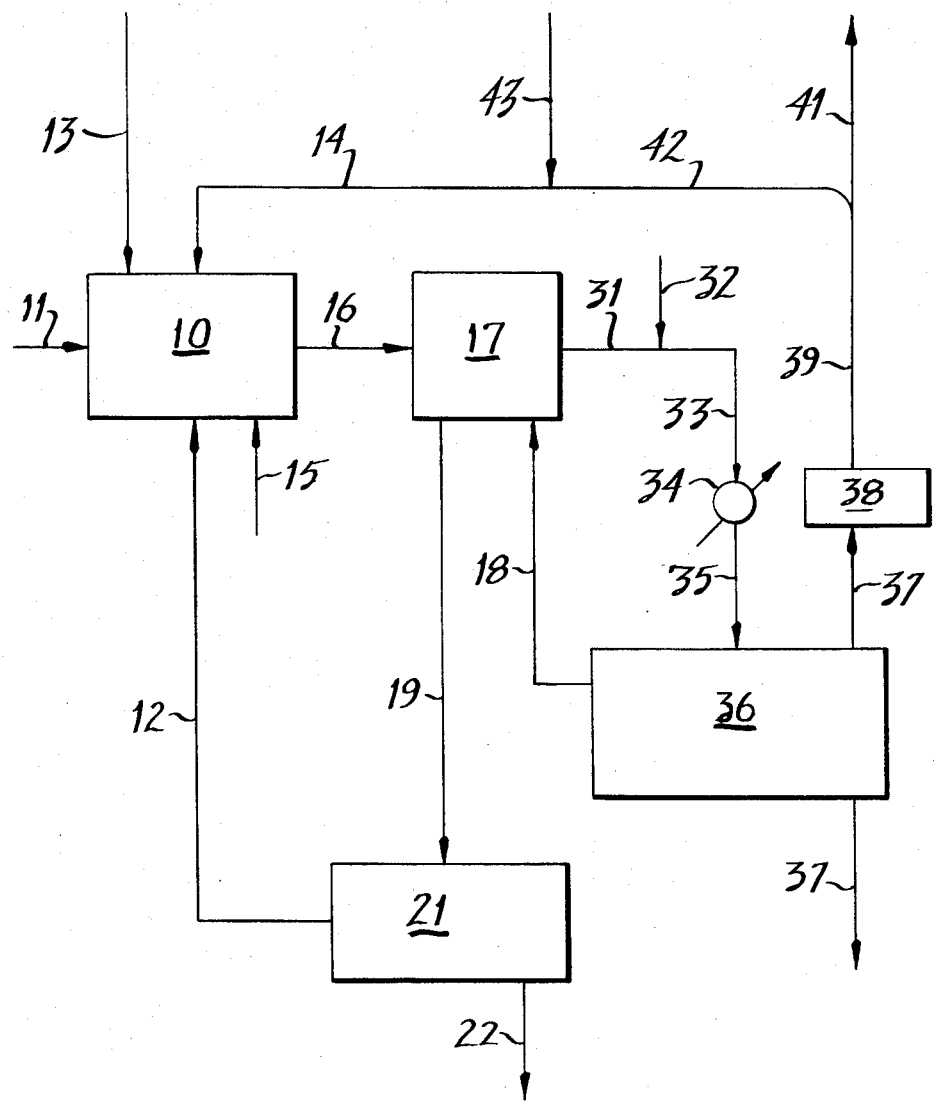

United States Patent [19]

Tsao

[11] Patent Number: 4,502,997
[45] Date of Patent: Mar. 5, 1985

[54] TREATMENT OF PURGE GAS

[75] Inventor: Utah Tsao, Jersey City, N.J.

[73] Assignee: The Lummus Company, Bloomfield, N.J.

[21] Appl. No.: 472,187

[22] Filed: Mar. 4, 1983

[51] Int. Cl.$^3$ .......................................... C07C 121/50
[52] U.S. Cl. ..................................... 260/465 C; 55/70
[58] Field of Search ........... 55/70; 260/465 C, 465 H; 423/352, 356

[56] References Cited

U.S. PATENT DOCUMENTS

| | | | |
|---|---|---|---|
| 2,756,841 | 7/1956 | Asendorf | 55/70 |
| 2,808,125 | 10/1957 | Buck et al. | 55/70 |
| 2,812,829 | 11/1957 | Marullo | 55/70 |
| 2,855,278 | 10/1958 | Adams et al. | 55/70 |
| 3,344,585 | 10/1967 | Hollowell | 55/70 |
| 4,134,910 | 1/1979 | Barchas et al. | 260/465 C |
| 4,246,417 | 1/1980 | Tsao | 203/96 |
| 4,251,235 | 2/1981 | Biermans | 55/70 |

Primary Examiner—Bernard Nozick
Attorney, Agent, or Firm—Elliot M. Olstein

[57] ABSTRACT

The invention relates to a process for treating purge gas including carbon dioxide, water vapor, organics and ammonia. In accordance with the invention, the purge gas is scrubbed with water to absorb ammonia and water is added to the scrubbed purge gas in an amount in excess of the amount required to dissolve the maximum amount of ammonium carbonate which can be formed from any ammonia and carbon dioxide present in the purge gas. The purge gas is subsequently cooled to condense the remaining organics and water and to provide a purge gas suitable for venting.

16 Claims, 2 Drawing Figures

TREATMENT OF PURGE GAS

This invention relates to the treatment of a vent gas to recover ammonia and organics therefrom.

For example, in the production of nitriles by oxidative ammonolysis (ammoxidation), the effluent from the reaction zone includes non-condensable gases, such as nitrogen, carbon monoxide and carbon dioxide. In order to prevent an excessive buildup of such non-condensables, the non-condensable gases must be separated and purged or vented from the system.

In the production, for example, of isophthalonitrile, the vapor to be purged or vented from the system includes in addition to nitrogen, carbon dioxide and carbon monoxide, some traces of hydrogen cyanide and nitrile compounds. As a result, the purge stream is generally cooled and scrubbed with water to recover ammonia and the organic feed prior to venting.

Thus, for example, the vent gas may be initially contacted with water in an absorber to absorb any ammonia present in the vent gas, with the top or overhead temperature of the absorber generally being maintained above 50° C. in order to avoid salting out or precipitation of ammonium bicarbonate in the absorber. After the absorption, the overhead vapor is cooled to recover any organics present in the vent gas.

In some cases, if the absorption operation is upset or the absorption water is not properly stripped of ammonia prior to use in the absorber, some ammonia will be present in the gas removed in the overhead line from the absorber. Since carbon dioxide and water vapor are present in such gas, in such a case, ammonium bicarbonate can precipitate in the vent line and result in plugging of the line. As a result, the overhead gas from the absorber is not cooled for maximum recovery of organic feed material in order to prevent the possibility of ammonium bicarbonate precipitation in the vent line.

The present invention is directed to providing an improvement in the recovery of organics and ammonia from a purge gas.

In accordance with one aspect of the prevent invention, a purge gas from a plant, which includes carbon dioxide, water vapor, organics and ammonia, is scrubbed with water, and preferably also with a portion of the organic feed to the plant, to absorb ammonia in the water and organics in the organic feed portion. Subsequent to the absorption, water is added to the scrubbed purge gas in an amount in excess of the amount required to dissolve the maximum amount of ammonium bicarbonate which can be formed from any ammonia and carbon dioxide present in the purge gas, followed by cooling of the purge gas to condense remaining organics and water therefrom. The thus treated gas may then be vented from the system.

In accordance with a particularly preferred embodiment, the purge gas is cooled after the absorption and water addition by indirect heat exchange with liquid ammonia feed to the plant.

The organics employed for scrubbing the purge gas, and those recovered from the purge gas, may be recycled to the reaction zone of the plant. Similarly, ammonia recovered from the purge gas may also be recycled to the reaction zone of the plant.

Figure 2:
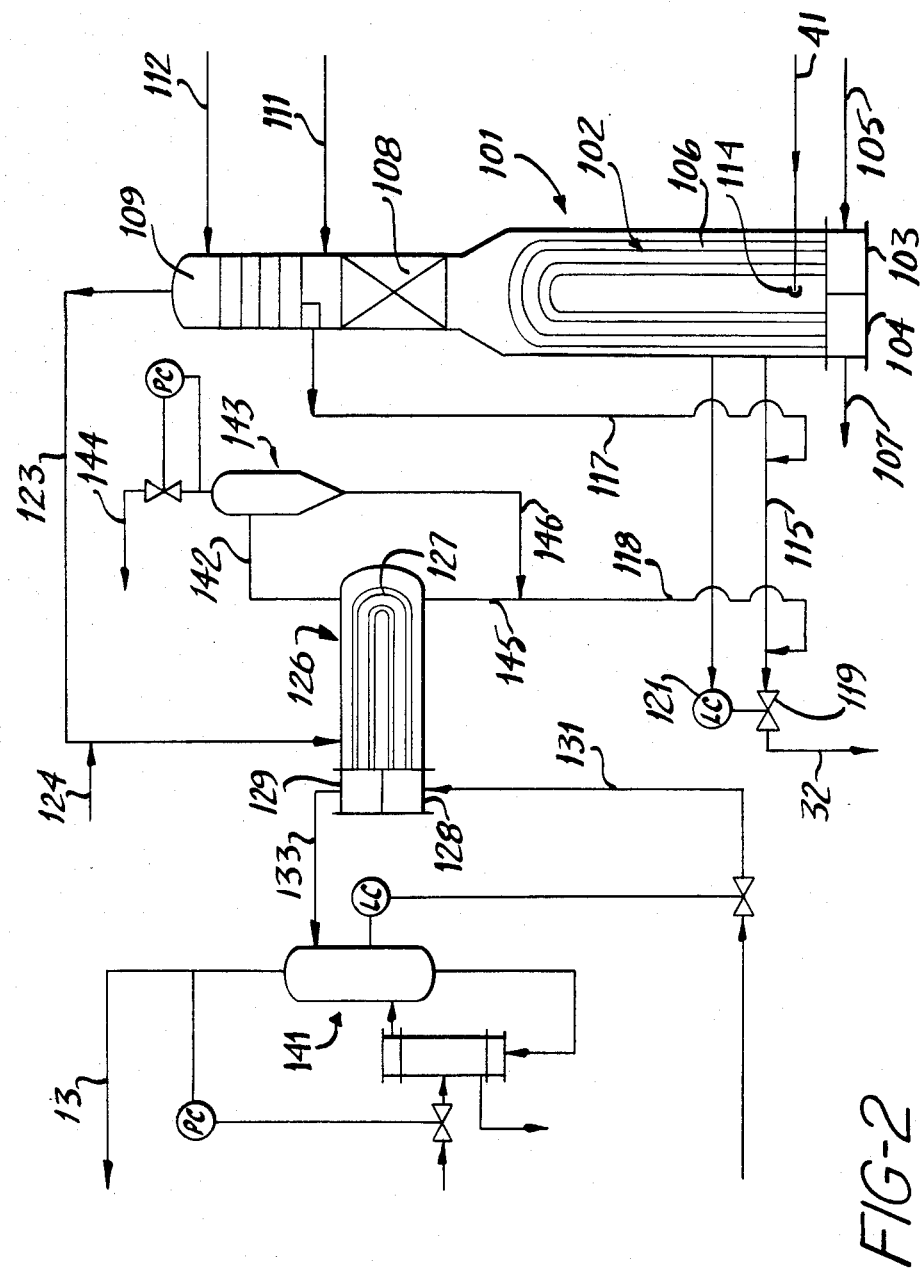

The invention will be further described with respect to a preferred embodiment thereof, illustrated in the accompanying drawings, wherein:

FIG. 1 is a simplified schematic flow diagram of a representative nitrile production process to which the present invention is directed; and FIG. 2 is a simplified schematic diagram of a system for treating a purge gas from the nitrile production in accordance with the invention.

The preferred embodiment will be described with respect to the production of isophthalonitrile from m-xylene; however, it is to be understood that the scope of the invention is not to be limited thereby.

Referring now to FIG. 1 of the drawings, organic feed, in particular m-xylene, is introduced into a reaction zone 10 through line 11. In addition recycled organics, such as m-xylene, tolunitrile, and benzonitrile, are introduced into the reaction zone 10 through line 12. The reaction zone is also provided with fresh feed ammonia through line 13 and recycled ammonia through line 14.

Oxygen is provided to the nitrile production zone through line 15.

In a typical process, the nitrile is produced by use of a supported vanadium oxide catalyst, with the catalyst being preferably oxidized with oxygen in a first reaction zone, and the oxidized catalyst employed for producing the isophthalonitrile by reaction between ammonia and organics.

Such a process and catalyst is described, for example, in U.S. Pat. No. 4,092,271.

In view of the fact that the nitrile production may be readily accomplished by those skilled in the art, no further details in this respect are deemed necessary for a complete understanding of the invention.

A reaction effluent, which includes isophthalonitrile, unreacted m-xylene, reaction intermediates (such as toluonitrile) ammonia, carbon oxides, nitrogen, water vapor, hydrogen cyanide, as well as heavier materials, is withdrawn from nitrile production zone 10 through line 16 for introduction into a quench zone, schematically generally indicated as 17. In the quench zone 17, effluent is contacted with an organic quench liquid introduced through line 18. The quench zone 17 is operated in a manner such as to quench heavier organics (including isophthalonitrile product) from the reaction effluent, without condensation of water.

The quenched organics, as well as any unvaporized quench liquid is withdrawn from the quench zone 17 through line 19 for introduction into a recovery zone, schematically generally indicated as 21. In recovery zone 21, reaction product is recovered through line 22, and recycle feed and intermediates are recovered through line 12 for introduction into the nitrile production zone 10.

Uncondensed effluent is withdrawn from quench zone 17 through line 31, combined with liquid recovered from the purge gas treatment, in line 32, obtained as hereinafter described, and the mixture in line 33 is passed through a condensor 34 for condensing water and organics therefrom, with the gas-liquid mixture from condensor 34, in line 35, being introduced into a separation zone 36 in order to separate condensed liquid from uncondensed gas.

Condensed organics are withdrawn from separation zone 36 through line 18 for recycle to the quench zone 17, as hereinabove described. Condensed aqueous phase is withdrawn from the separation zone 36 through line 37 for recovery of ammonia therefrom.

Uncondensed material, which is comprised of ammonia, some organics, carbon dioxide, carbon monoxide, nitrogen and water vapor is withdrawn from separation zone 36 through line 40 and compressed in compressor 38. The compressed gas in line 39 is divided into a purge portion in line 41, and a recycle portion in line 42, which contains a high portion of ammonia. The recycle gas in line 42 is combined with ammonia in line 43 recovered from the aqueous phase in line 37, and the combined stream in line 14 is recycled to the nitrile production.

The purge gas in line 41 is treated in accordance with the present invention, as hereinafter described in more detail with reference to the embodiment illustrated in FIG. 2.

Referring now to FIG. 2, the purge gas in line 41 is introduced into a combined absorber cooler, schematically generally indicated as 101. The lower portion of the combined absorber cooler 101 is a vertical U-shaped heat exchanger, generally indicated as 102, comprised of U-shaped heat exchange tubes 106 having one end connected to an inlet header 103, and the other end to an outlet header 104. The inlet header is provided with cooling water through line 105, which flows through the U-shaped tubes 106 to outlet header 104 where the water is withdrawn through line 107.

The upper portion of absorber cooler 101 is a two-section absorber, with the lower portion being provided with packing 108, and the upper portion with suitable trays 109.

The lower absorption section, which contains packing 108, is provided with water essentially free of ammonia, which essentially ammonia free water is introduced through line 111.

The upper portion of the absorber, which includes trays 109, is provided with organic absorption liquid, and in particular a portion of the m-xylene feed, through line 112.

The purge gas in line 41 is introduced into the heat exchanger portion 102 through a suitable sparger schematically generally indicated as 114.

The purge gas in line 41 includes carbon dioxide, as well as ammonia, and as a result, in the absorption of ammonia, by the water, the amount of carbon dioxide which is absorbed should be kept to a minimum in that any absorption of carbon dioxide in the water will increase the amount of carbon dioxide which must be separated from ammonia in the ammonia recovery section of the plant for recovering ammonia from the aqueous phase in line 37. Accordingly, it is desirable to vent as much of the carbon dioxide as possible in the purge gas; therefore, the liquid level in the heat exchange section 102 is maintained as low as possible, and packing 108 further functions to minimize the amount of carbon dioxide absorbed in the water.

The water which is introduced into the packed section 108 through line 111 showers down on to the top of the U-shaped tubes 106, which tubes function as a falling film cooler. The ammonia in the purge gas introduced through line 41 is absorbed into the liquid film falling down on the tube surface, and the heat of absorption is simultaneously removed by the cooling water which flows through the tubes 106. The liquid residence time in the lower section is minimized, thereby minimizing the absorption of carbon dioxide.

Water containing absorbed ammonia is withdrawn from the lower portion of the heat exchange section 102 through line 115.

The gas which exits from the packing 108 is then contacted with a portion of the organic feed which is introduced through line 112, and which flows across the trays 109. The organics introduced through line 112, after flowing across trays 109, are withdrawn from the tray section through line 117, and combined with the water which contains absorbed ammonia, carbon dioxide, and some organics in line 115, with the combined stream being further combined with additional organics in line 118, for eventual return to separator 36 through line 32. Line 32 is provided with an appropriate valve 119 and level controller 121 for maintaining the desired liquid level in the lower portion of the heat exchanger portion 102 of the combined absorber cooler 101.

A scrubbed gas is withdrawn from the combination absorber cooler through line 123, and such gas is generally withdrawn at a temperature of 75° C. to 45° C., and preferably from 55° C. to 50° C. The gas includes nitrogen, carbon dioxide, carbon monoxide, water vapor, xylene, and may further include traces of nitriles and ammonia. The gas in line 123 is combined with water, essentially free of ammonia, which is provided through line 124. The water is provided in an amount which is in excess of the amount required to dissolve the maximum potential amount of ammonium bicarbonate which could be formed in the vent line. This water functions to reduce the ammonia content in the gas, and further to prevent the salting out of ammonium carbonate in the chilling system in case there is an accidental presence of ammonia.

The purge gas, now containing water, in line 125, is introduced into a chiller, schematically generally shown as 126. As particularly shown, the chiller 126 is in the form of a U-tube heat exchanger having tubes 127, with the inlet ends of tubes 127 being connected to inlet header 128 and the outlet end of tubes 127 being connected to an outlet header 129. The vent gas in line 125 is introduced into the shell side of the heat exchanger.

The inlet header 128 is provided with liquid ammonia feed to the nitrile production through line 131.

The purge gas is further cooled in chiller 126 by indirect heat transfer with the ammonia flowing through the tubes 127, with the cooling of the purge gas resulting in condensation of water and any further organics remaining in the purge gas.

Partially vaporized ammonia is withdrawn from the outlet header 129 through line 133 for introduction into the ammonia reboiler system for vaporizing the remaining portion of liquid ammonia. The reboiler system is schematically generally shown as 141, with the vaporized ammonia feed being withdrawn from the reboiler 141 through line 13 for introduction into the nitrile production zone.

The uncondensed portion of the purge gas, which may include some condensed mist, is withdrawn from chiller 126 through line 142, and introduced into an entrainment separator, schematically generally indicated as 143 for removing entrained mist. The purge gas, free of entrained mist, is withdrawn from the entrainment separator 143 through line 144 for subsequent venting from the system.

Condensed material from chiller 126, in line 145, as well as separated mist in line 146, are combined in line 118 for return to the nitrile production system through line 32, as hereinabove described.

Thus, the organics, as well as ammonia present in the purge gas are recovered therefrom, with the organic materials eventually being recycled to the nitrile production through the quench system. The ammonia recovered from the purge gas is eventually recycled to the nitrile production by recovery of the ammonia from the aqueous phase recovered in line 37, with such recovery being accomplished by procedures known in the art, for example by the method described in my U.S. Pat. Nos. 4,342,735 and 4,246,417.

EXAMPLE

In a plant producing 1900 lb/hr isophthalonitrile the purge stream 41 will be 55,000 SCFH at 25 psig and 165° which contains 470 lb/hr m-xylene, 1.5 lb/hr benzonitrile, 1 lb/hr m-toluonitrile, 1600 lb/hr ammonia, 50 lb/hr carbon dioxide, 130 lb/hr carbon monoxide, 870 lb/hr nitrogen and 175 lb/hr water. After the gas stream passes through the absorber cooler 101 it is scrubbed with 3,000 lb/hr of process water at 53° C. from line 111. The gas is cooled down to 55° C. All the ammonia and a part of the carbon dioxide is absorbed by the water and a large portion of the organics and the water vapor is condensed. The volume of the gas stream is reduced to 14,800 SCFH containing 76 lb/hr xylene, 0.24 lb/hr benzonitrile, 0.15 lb/hr m-toluonitrile, 25 lb/hr carbon dioxide, 130 lb/hr carbon monoxide, 870 lb/hr nitrogen and 38 lb/hr water. Using 100 lb/hr of xylene feed for stream 112 as absorption liquid and 6 trays in the absorber, the amounts of benzonitrile and m-toluonitrile in the vent leaving the absorber would be reduced to less than 10 ppm by weight. To prevent any salting out of ammonium carbonate salt in the chilling system during any ammonia breakthrough 100 lb/hr of process water is injected in the vent line before the gas is chilled in the chiller 126 to 2° C. The amount of xylene condensed amounts to 71 lb/hr. At a m-xylene cost of $0.36/lb the cost of xylene recovered by chilling amounts to $204,000/yr. The amount of nitriles left in the vent gas would be less than 1 ppm.

By proceeding in accordance with the present invention, it is possible to cool the purge gas, after absorption of ammonia therefrom, to a temperature in the order of from 20° C. to 0° C., and preferably from 5° C. to 2° C. (for example in chiller 126) to enable maximum recovery of organics from the purge gas for recycle to the nitrile production system.

Moreover, potential plugging in the vent line is eliminated.

Furthermore, organic compounds, such as nitriles, are effectively removed from the purge gas so that the purge gas may be vented from the system through an ordinary boiler for incineration.

Furthermore, the hydrogen cyanide content of the purge gas is reduced.

Although the invention has been described with respect to a preferred embodiment, it is to be understood that the embodiment may be modified within the spirit and scope of the invention.

Thus, for example, in some cases, the organic absorption liquid, which is a part of the organic feed, and which is introduced into the combination cooler-absorber 101 through line 112 may be omitted, whereby the purge gas is only contacted with an aqueous absorption liquid. In such an embodiment, organics which remain in the purge gas would be recovered in the chiller.

Similarly, although the scrubbed purge gas is preferably cooled by indirect heat transfer with liquid ammonia feed in that such a procedure reduces energy requirements, it is to be understood that the scrubbed purge gas may be cooled in a manner other than as particularly described.

These and other modifications will be apparent to those skilled in the art from the teachings herein.

The present invention is particularly advantageous in that it maximizes recovery of ammonia from the purge gas, while minimizing the amount of carbon dioxide which is absorbed by the water. Furthermore, the present invention permits maximization of recovery of organics from the purge gas, while minimizing, if not eliminating, the possibility of ammonium bicarbonate precipitation and plugging of vent lines. Moreover, by such treatment, the organic nitriles content of the vent gas can be less than 1 ppm. In addition, energy requirements can be reduced by vaporizing ammonia feed by indirect heat transfer cooling of the scrubbed purged gas.

The present invention is also advantageous in that it is applicable to the production of a wide variety of nitriles, although the preferred embodiment has been described with respect to the production of isophthalonitrile. Thus, for example, the process is also applicable to the production of nitriles by amoxidation of alkyl substituted aromatic hydrocarbons, in general, as well as the amoxidation of aliphatic compounds, such as olefinic hydrocarbons, at least three carbon atoms, such as propylene and isobutylene to produce acrylonitrile and methacrylonitrile, respectively.

Similarly, the process is also applicable to the amoxidation of heterocyclic compounds, and in particular alkyl substituted pyridines in that such pyridines can be converted to nicotinonitrile.

It is also to be understood that the process is applicable to other processes in which ammonia and organics may be present in a purge gas and is not limited to nitrile production.

These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

I claim:

1. A process for treating a purge gas containing carbon dioxide, water vapor, condensable organic and ammonia, comprising:
   scrubbing the purge gas with water, said scrubbing absorbing ammonia from the purge gas; recovering a scrubbed purge gas; adding water to the scrubbed purge gas in an amount in excess of the amount required to dissolve the maximum amount of ammonium bicarbonate which can be formed from any ammonia and carbon dioxide present in the purge gas to prevent salting out of ammonium bicarbonate; and cooling the scrubbed purge gas to a temperature from 0° C. to 20° C. to condense the condensable organic and water therefrom and provide a purge gas suitable for venting.

2. The process of claim 1 wherein the scrubbed purge gas, prior to adding water, is at a temperature of from 45° to 75° C.

3. The process of claim 2 wherein the cooling of the scrub bed purge gas is to a temperature of from 2° C. to 5° C.

4. In a process for producing an aromatic nitrile from an aromatic hydrocabon and ammonia wherein there is recovered a purge gas including carbon dioxide, water vapor, condensable organic convertible to the aromatic nitrile, and ammonia, the improvement comprising:

scrubbing the purge gas with water, said scrubbing absorbing ammonia; recovering a scrubbed purge gas; adding water to the scrubbed purge gas in an amount in excess of the amount required to dissolve the maximum amount of ammonium bicarbonate which can be formed from any ammonia and carbon dioxide present in the purge gas to prevent salting out of ammonium bicarbonate; cooling the scrubbed purge gas to a temperature of from 0° C. to 20° C. to condense condensable organic convertible to the aromatic nitrile and water therefrom and provide a purge gas suitable for venting; and employing organic convertible to nitrile and ammonia recovered from the purge gas in the production of the aromatic nitrile.

5. The process of claim 4 wherein the purge gas is recovered from a process for producing a nitrile.

6. The process of claim 2 wherein the purge gas is also scrubbed with a portion of organic feed to the nitrile production to absorb organic prior to said adding water.

7. The process of claim 6 wherein the purge gas is cooled by indirect heat transfer with ammonia to be employed as feed to the nitrile production.

8. The process of claim 7 wherein scrubbing of purge gas to remove ammonia is effected by means of water in in the form of a falling film on heat exchanger tubes.

9. The process of claim 8 wherein organics and absorbed ammonia recovered from the purge gas are recycled to the nitrile production.

10. The process of claim 4 wherein the aromatic nitrile is a phthalontrile and the aromatic hydrocarbon is a xylene.

11. The process of claim 10 wherein the scrubbed purge gas is at a temperature of from 45° to 75° C.

12. The process of claim 11 wherein the cooling of the scrubbed purge gas is to a temperature of from 2° to 5° C.

13. The process of claim 12 wherein the cooling of the scrubbed purge gas is by indirect heat transfer with ammonia to be employed as feed to the nitrile production.

14. The process of claim 13 wherein prior to adding water, the purge gas is also scrubbed with a portion of organic feed to the nitrile production to absorb organics.

15. The process of claim 14 wherein the scrubbing of purge gas to remove ammonia is effected by means of water in the form of a falling film on heat exchanger tubes.

16. The process of claim 14 wherein the nitrile is isophthalonitrile and the xylene is m-xylene.

* * * * *